United States Patent [19]

Hardy et al.

[11] Patent Number: 4,681,853
[45] Date of Patent: Jul. 21, 1987

[54] PERFUSION SLIT CHAMBER FOR FILTER-BOUND SAMPLE ANALYSES

[76] Inventors: Kenneth J. Hardy, 2132-16th Ave., San Francisco, Calif. 94106; Michael G. Whitesides, 654 Minnesota St., Daly City, Calif. 94107

[21] Appl. No.: 790,586

[22] Filed: Oct. 23, 1985

[51] Int. Cl.$^4$ .................................... C12M 1/40
[52] U.S. Cl. ................................ 435/288; 435/285
[58] Field of Search .............. 435/287, 288, 311, 285; 210/443, 445, 451, 453, 455, 456

[56] References Cited

U.S. PATENT DOCUMENTS

| | | | |
|---|---|---|---|
| 1,430,234 | 9/1922 | Keithline | 210/451 |
| 2,389,185 | 11/1945 | Dick | 210/445 |
| 4,009,714 | 3/1977 | Hammer | 210/445 |
| 4,324,658 | 4/1982 | Esmond | 210/456 |

OTHER PUBLICATIONS

Turbo Blot TM brochure by American BioNuclear.
Omni Blot TM brochure by American BioNuclear.

*Primary Examiner*—Larry Jones
*Assistant Examiner*—Noah Kamen
*Attorney, Agent, or Firm*—Limbach, Limbach & Sutton

[57] ABSTRACT

A membrane is supported in a chamber for treating the faces of the membrane with a fluid. The chamber is made from two cover plates clamped together with interior support pegs and valve connections for introducing and removing treatment fluid.

3 Claims, 6 Drawing Figures

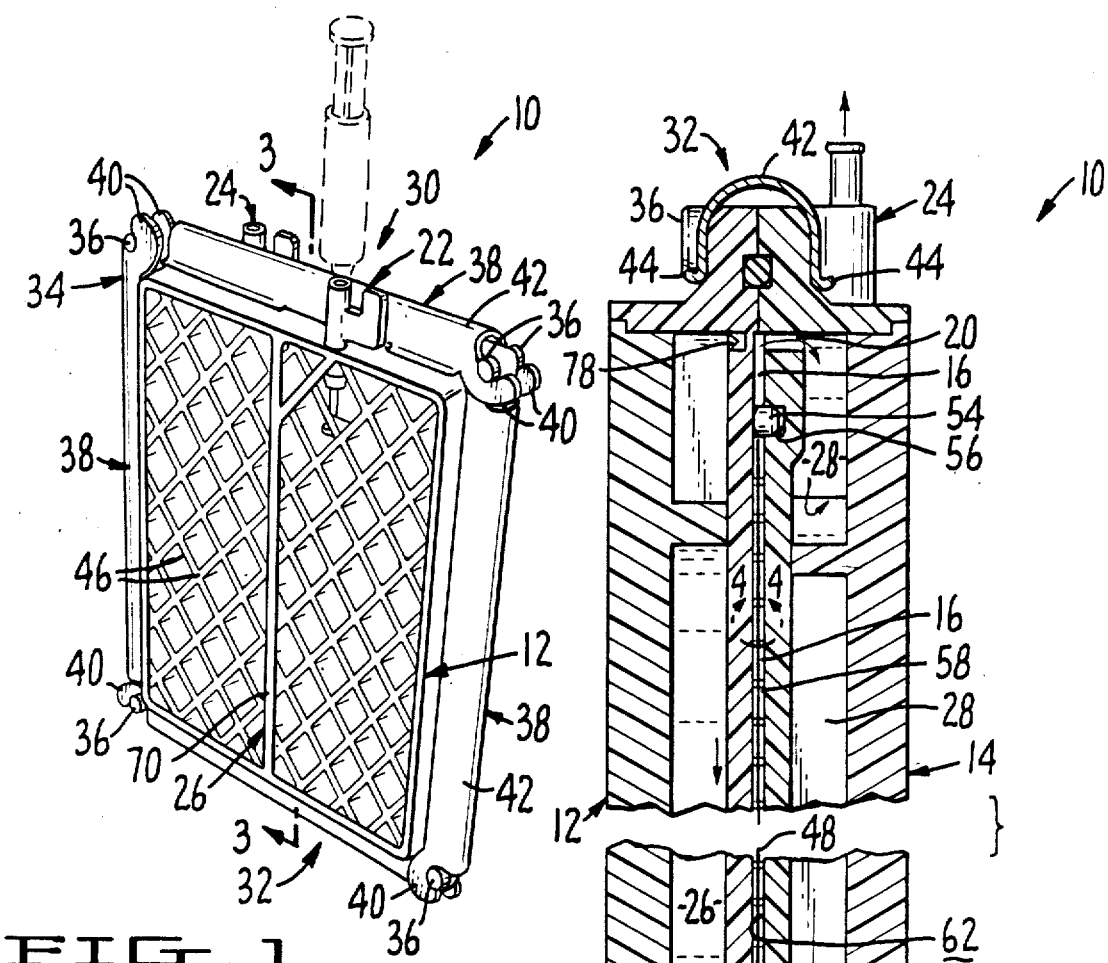
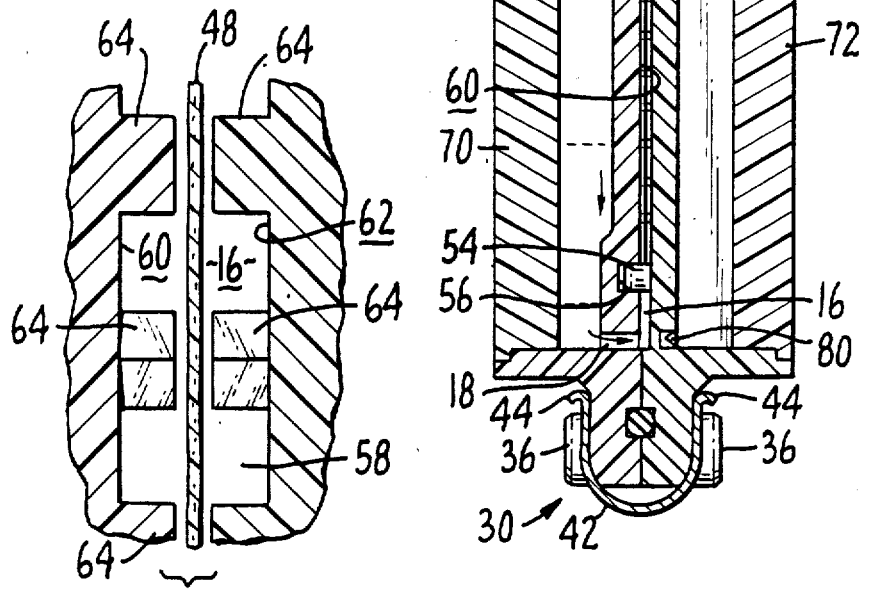
FIG. 1.
FIG. 4.
FIG. 3.

PERFUSION SLIT CHAMBER FOR FILTER-BOUND SAMPLE ANALYSES

BACKGROUND OF THE INVENTION

This invention relates to an apparatus and method for analyzing filter-bound samples and, more particularly, to a low volume perfusion slit chamber for treating and/or developing nucleotide and protein-bound membranes.

Many current methodologies for the high resolution analyses of proteins, nucleic acids, and polynucleotides immobilize samples on thin filter membranes and subsequently analyze the filters using immunologic or recombinant hybridization technologies.

Several years ago, it was found that singlestranded DNA binds very tightly to membrane filters made of nitrocellulose, and that such filters failed to bind either double-stranded DNA or RNA. This phenomenon can be used, for example, to determine the presence of specific complementary base sequences in single-stranded DNA by binding one type of single-stranded DNA to a nitrocellulose filter and reacting the bound single-stranded DNA with labeled, singlestranded DNA or RNA. Where such base sequences are present, the second type of single-stranded DNA or of RNA binds to the filter-bound single-stranded DNA. The presence of double-stranded DNA or a DNA-RNA complex bound to the nitrocellulose sheet can be detected utilizing the label attached to the second type of single-stranded DNA or RNA. If, for example, a radioactive label is used, the presence of a double-stranded DNA or DNA-RNA complex can be detected by exposing x-ray films with the nitrocellulose sheet and developing the x-ray films.

A wide variety of analytical techniques have since been developed utilizing this basic phenomenon. See, e.g., D. Freifelder, *Molecular Biology*, pp. 123-124 and 418-425 (1983). For example, when single-stranded polynucleotides (DNA or RNA) are separated electrophoretically in polyacrylamide gels or other media, the separated polynucleotides and polynucleotide fragments can be transferred or "blotted" from the polyacrylamide gels onto nitrocellulose membranes or sheets. The separated single-stranded DNA, bound to the sheet, can now be localized by reacting the bound single-stranded DNA with specific sequences or fragments of single-stranded DNA or RNA that have previously been labeled for detection. Possible labels include fluorescent and other chemical labels, as well as radioactive labels, such as $^{32}P$-phosphate labels and $^{14}C$ labels.

Similar technologies have been developed for the localization of electrophoretically separated proteins and/or detection of proteins or samples of genetic material dotted onto filter membranes for screening.

Such methods all require rigid control of reaction temperatures at each step and accurately controlled development times. Because of the complex kinetics of chemical interaction involved, as well as the fact that many of the reagents, such as radioactively labled polynucleotides, are rare and/or difficult to isolate or produce in large quantities, the development reactions must be carried out in minimum effective volumes. This, in turn, requires optimization of the efficiency of the interaction between the filter-bound sample and reagents. In addition, a wide range of reagent types and conditions are routinely used. Often, the filters are variable in size, shape, and type, are fragile, and are difficult to handle.

Filter analyses are usually done (with agitation) in open, large-volume containers or, in the case of nucleic acid analyses, in crude, heat-sealed plastic bags. For most purposes, such arrangements are cumbersome and wasteful of reagents, and are inefficient in terms of both the amounts of reagents required and in the time required to complete a particular reaction. Where the labels used include high specific activity radioisotopes, such systems may also be very hazardous. The operator may be exposed to significant radiation while handling such equipment, which is prone to leakage and spillage of radioactive solutions. It is also difficult, at best, to properly dispose of all radioactive materials used in such systems due to spillage, inconvenience of the operations which must be performed, and the relatively large quantities of radioactive material which must be handled and disposed of; such systems thus also are a potential source of environmental hazard.

The plastic bags used frequently in nucleic acid hybridizations are difficult to work with, are prone to leakage, and require agitation to maximize filter/reagent interactions. Such bags are not reusable, and do not afford any significant protection to the often fragile filters being analyzed. Due to the flexibility of the plastic bags, reagent distribution is often uneven, since the positions of the filters within such plastic bags are not readily controllable. Further, such plastic bags systems require reopening and resealing after every reagent change and are effectively useless for washing steps which require large volumes of wash reagents and agitation of the filters and reagents. While such plastic bag systems allow the exclusion of air bubbles from the filter/reagent interface, and complete immersion of the filters with a relatively small volume of reagent, both plastic bag development systems and development systems utilizing large-volume containers have proven inconvenient, inefficient, non-reproducible, and often unsatisfactory for routine use in the analysis of filter-bound samples.

SUMMARY OF THE INVENTION

An apparatus and method for the localization, development, and analysis of filter-bound samples is disclosed. The apparatus of the present invention generally includes two cover plates, at least one of which has a shallow, generally rectangular recess formed on one side thereof. The two cover plates are matable to form a thin treatment chamber to sealingly enclose a filter or membrane sheet on which single-stranded DNA or other substance of interest has been deposited. The apparatus further includes reagent ports for introducing and alternatively withdrawing reagents from the treatment chamber, and valve assemblies to control the reagent flows.

In the preferred apparatus of the invention, a plurality of filter support pegs are affixed to the opposing interior surfaces of the treatment chamber to position the filter or membrane sheet away from the opposing treatment chamber walls, thereby allowing free flow of reagent along each side of the filter or membrane sheet. Typically, the treatment chamber has dimensions of about 15 cm by about 18 cm by about 0.05 cm; the filter support pegs typically extend into the treatment chamber about 0.015 to about 0.018 cm, leaving a gap of about 0.01 cm to 0.02 cm for placement of the filter or membrane sheet. The treatment chamber thus has a very small volume but very efficient solution-filter sheet contact.

Preferably, the cover plates are provided with pairs of interlocking baffles and slots arranged near either end of the treatment chamber to distribute the introduced reagents evenly over the width of the treatment chamber. Preferably, each baffle is located between the corresponding reagent port and the positioned filter or membrane sheet.

The preferred embodiment of the apparatus also includes reagent paths for fluidly communicating the reagents from the valve assemblies to the corresponding reagent ports, clamping assemblies for releasably securing the cover plates together, and heat exchange fins on the outside of the cover plates to ensure rapid and effective temperature equilibration of the apparatus.

The preferred method according to the invention includes placing a filter or membrane sheet with bound DNA or other substances of interest between the cover plates and clamping the apparatus together to enclose the filter or membrane sheet. Sequentially, prehybridization solution, hybridization solution including a radioactively labeled reagent, and wash solutions of increasing stringency are introduced into the reaction chamber, preferably entirely with syringes in cooperation with syringe fittings mounted to the valve assemblies in controllable fluid communication with the reagent ports. The treated, labeled filter or membrane sheet may then be removed for detection of the labels, and hence the substance of interest by known x-ray film exposure and/or other development methods.

The apparatus according to the present invention and the method for using the apparatus eliminate the majority of the problems associated with the analysis of a filterbound sample using reagent-filled plastic bags and other reaction vessels, while improving and facilitating the analysis of filter-bound nucleic acids and proteins. The preferred embodiment of the reusable, fully perfusable reaction slit chamber of the invention is compatable with the entire range of conditions, filters, and reagents used in current immunologic and recombinant analytic technologies. The apparatus minimizes internal fluid volumes, eliminates air bubbles, and allows rapid insertion and removal of filters. In addition, the apparatus and its use dramatically improve the most important parameter in all such analyses, the homogenous, unobstructed filter/reagent reaction at the interface between the filter and the reagent. This optimization is accomplished by the combination of the filter support pegs, which hold the filter membrane in position away from either side of the treatment chamber, the internal bilaminar flow generation system, and the liquid addition channels or reagent paths. Due to the highly efficient filter/reagent interactions and the design of the apparatus according to the invention, significant reductions in the volumes of the reagents required, radioactive wastes, and reaction times required are achieved. With the apparatus and method of the present invention, significant reduction in signal background is routinely accomplished, and the variability of results between successive experiments is minimized.

The apparatus is readily assembled and operated using externally mounted syringe fittings. The filters are positioned and protected reproducibly within the treatment chamber, which can accommodate a wide range of filter types, sizes, and shapes. The apparatus is fully self-contained; sequential addition and removal of reagents are readily accomplished without manipulation of the filter, transfer of the filter from one container to another, or the need for external tubing, pumps, or vacuum equipment. The apparatus is self-cleaning and is decontaminated during filter wash cycles.

With the apparatus and method of the present invention, environmental hazards are minimized. The cover plates of the preferred apparatus effectively shield the operator from beta emissions during handling and incubation, and the radioactive reagents necessary are conveniently added and removed from the preferred perfusion slit chamber without danger of spillage and, in small volumes, ready and convenient for disposal. The external syringe ports of the preferred embodiment facilitate safe and efficient handling of hazardous liquids.

The apparatus and method of the present invention can be used for a wide variety of types of filters and membranes, including both nitrocellulose and nylon based filters, some impregnated with various substances and resins. The apparatus and method of the invention can conveniently be used with a wide variety of analytical techniques, including, but not limited to, DNA hybridization techniques, DNARNA hybridization techniques, autoradiographic techniques, the southern blot technique used with DNA electrophoresis, the northern blot technique used with RNA electrophoresis, and the western blot technique used in immunoassay of proteins. In addition, the apparatus and method provide a convenient technology for genetic disease screening, especially of the type termed "Restriction Fragment Length Polymorphism" (RFLP). RFLP assays are currently being used for detection of Huntingtons Chorea, sickle cell disease, and other diseases. RFLP assays are also being devised as prenatal screening tests, e.g., Tay Sachs disease, phenylketonuria, galactosemia, sex determination, and other factors.

The preferred apparatus according to the invention can be principally manufactured from plexiglass or polysulfone; such plastics are readily machinable and/or moldable, readily withstand the often elevated temperatures required for incubation and reaction, do not interact with any presently used or known reagents for analyzing filter-bound samples, and do not readily adsorb DNA, RNA, or protein. Other plastics having similar properties may be utilized as necessary. For example, silicon rubber is conveniently used for the required O-rings and gaskets, and the valve assemblies can be fabricated using Delrin. The preferred apparatus of the present invention incorporates no metal parts which might react with the reagents used. Such reactions are to be avoided since corroded metal parts interfere with the operation of the apparatus and use of the method; leached metals can also cause degredation of the reagents and samples of interests.

A presently preferred membrane for use with the apparatus and method of the present invention is a treated nylon 66 membrane manufactured by Molecular Separations, Inc.; This filter does not contract and expand significantly when dried or moistened, respectively. Although it is more convenient for the operator to use such filter types, the apparatus and method of the present invention are not so restricted.

The above and other features and objects of the invention, and the operation and advantages of the invention, will be better understood and appreciated by those skilled in the art in view of the description of the preferred embodiment given below in conjunction with the accompanying drawings.

BRIEF DESCRIPTION OF THE DRAWINGS

FIG. 1 is a perspective view of the preferred perfusion slit chamber according to the invention, showing schematically the placement of a syringe in phantom.

FIG. 2 is an exploded perspective view of the preferred perfusion slit chamber according to the invention.

FIG. 3 is a cross-sectional view of the preferred perfusion slit chamber along section 3—3 of FIG. 1.

DETAILED DESCRIPTION OF THE PREFERRED EMBODIMENTS

The preferred perfusion slit chamber 10, according to the present invention, is shown assembled in perspective view in FIG. 1 and in the exploded perspective view in FIG. 2.

Figure 4:
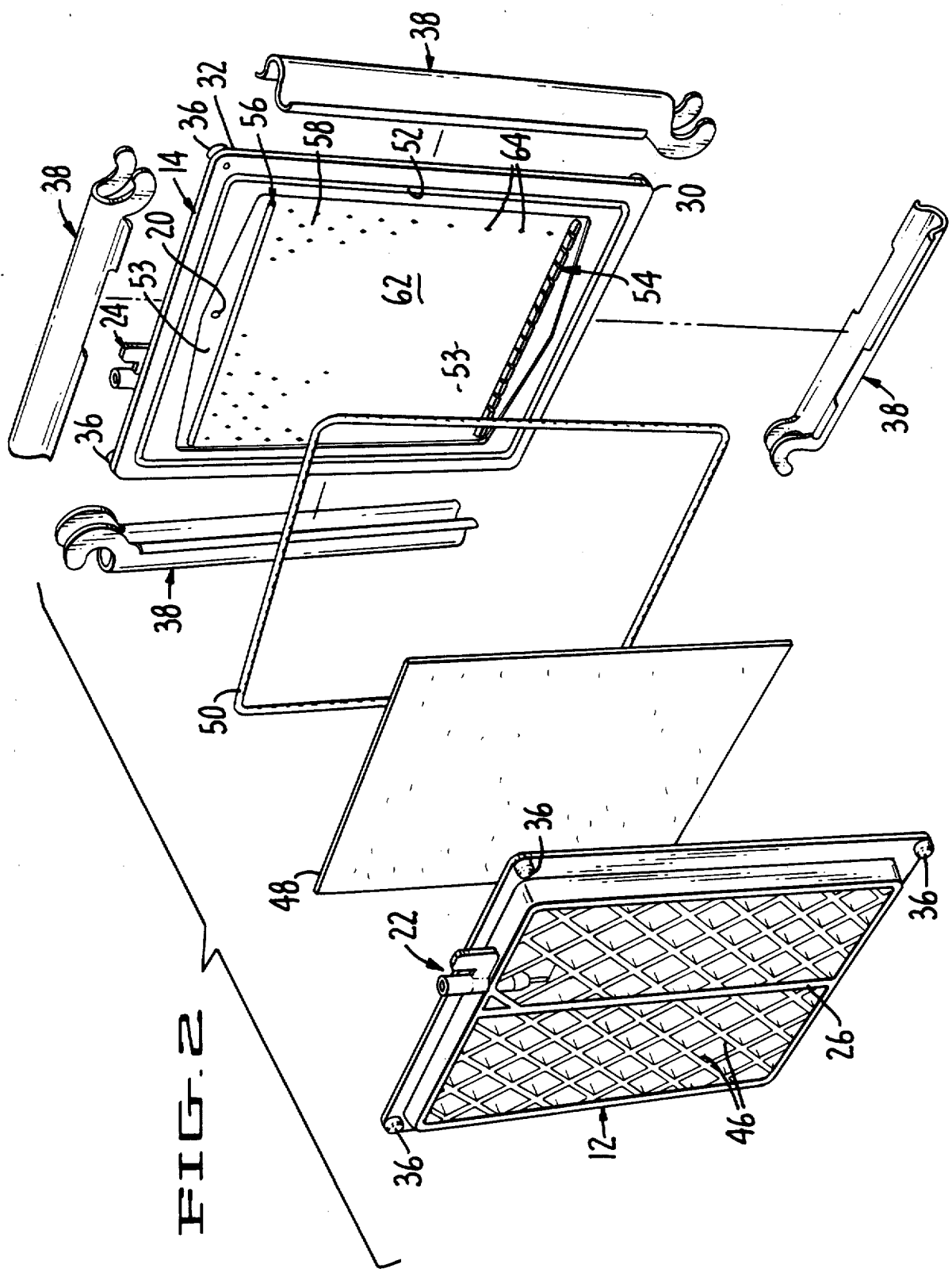
FIG. 4 is a detail view of the preferred perfusion slit chamber showing the membrane support pegs, taken in the region 4—4 of FIG. 3.

Referring principally to FIGS. 1 and 2, preferred perfusion slit chamber 10 generally includes first and second cover plates 12 and 14, matable to define therebetween a treatment chamber 16. Treatment chamber 16 will be described more fully below in conjunction with the description of FIGS. 3-5.

Perfusion slit chamber 10 also includes, in the preferred embodiment, first and second reagent ports 18 and 20 (FIG. 3), which allow fluid communication between treatment chamber 16 and the exterior of perfusion slit chamber 10. In the preferred embodiment of the invention, the flow of reagents through first and second reagent ports 18, 20 is controlled with valve assemblies 22, 24, which are, in turn, fluidly coupled to first and second reagent ports 18, 20 via first and second reagent paths 26, 28. In the preferred profusion slit chamber 10, first reagent port 18 is located near bottom 30 of perfusion slit chamber 10 and defined through first cover plate 12; second reagent port 20 is defined, near top 32, in second cover plate 14. As will be explained more fully below, it is convenient to form first and second reagent ports 18, 20 in different cover plates 12, 14 to faciliate the construction of reagent paths 26, 28 and the mounting of valve assemblies 22, 24. However, in alternate embodiments of the invention, first and second reagent ports 18, 20 could both be defined in a single cover plate 12 or 14. Similarly, it is convenient in the preferred perfusion slit chamber 10 to define one reagent port 18, 20 near bottom 30 and the other of reagent ports 18, 20 near top 32; however, in alternate embodiments of the apparatus according to the invention, other arrangements are possible and will be apparent to those skilled in the art. The arrangement of reagent ports 18, 20, as shown in FIG. 1, allow the optimum flow of reagents through treatment chamber 16.

For ease of handling and insertion of perfusion slit chamber 10 in a heated and temperature controlled water bath (not shown), it is convenient to mount first and second valve assemblies 22, 24 near top 32 so that valve assemblies 22, 24 can be positioned to extend above the water or fluid level of the heat bath. However, it is not necessary that both the valve assemblies 22, 24 be positioned either near the same end of perfusion slit chamber 10 or near top 32. Similarly, it is convenient to mount first and second valve assemblies 22, 24 on first and second cover plates 12, 14, respectively; however, first and second valve assemblies 22, 24 will be mounted on the same or different cover plates 12, 14 in accordance with the locations of the reagent ports 18, 20. First and second valve assemblies 22, 24 will be explained in greater detail below in conjunction with FIG. 5.

First and second reagent paths 26, 28 are constructed to connect first and second valve assemblies 22, 24 with first and second reagent ports 18, 20, respectively, to allow introduction and removal of reagents from treatment chamber 16.

Preferred perfusion slit chamber 10 also includes a plurality of clamping assemblies 34. In preferred slit chamber 10, four clamping assemblies 34 each include a pair of clamping posts 36 and a clamp 38. Each pair of clamping posts 36 is rigidly fixed to first and second cover plates 12, 14 and arranged to extend outward therefrom approximately colinerally. Clamping posts 36 are conveniently molded or constructed from the same piece of material as cover plates 12, 14 and provide mounting points and fulcrums for clamps 38.

Figure 6:
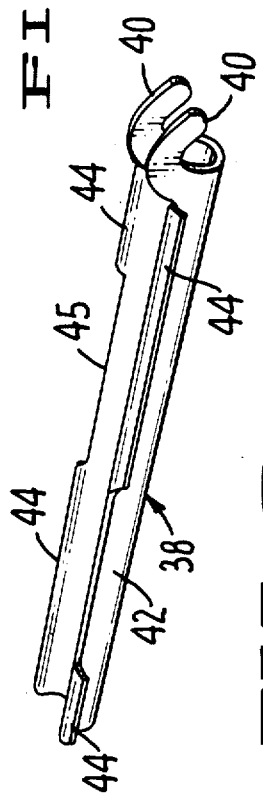
FIG. 6 is a perspective view of a clamp for use with the preferred perfusion slit chamber.

Each clamp 38 includes a pair of hook portions 40 and a clamp portion 42. A perspective view of the clamp 38 is shown in FIG. 6. Each hook portion 40 is shaped to partially encircle one of clamping posts 36; the respective hook portions 40 of a single clamp 38 are arranged to extend from clamp portion 42 in generally mutually parallel spaced apart relation; the distance between hook portions 40 is chosen to allow hook portions 40 to engage simultaneously the corresponding pair of clamping posts 36. Each clamp portion 42 has a generally C-shaped cross-section (clearly shown in FIG. 3) and a length corresponding, in the preferred embodiment, to the particular dimension of cover plates 12, 14. To clamp cover plates 12, 14, hook portions 40 are engaged to the corresponding clamping posts 36 and, in a lever-type motion, clamp portion 42 is advanced toward cover plates 12, 14 so that the opposing sides of the C-shaped cross-section of clamp portion 42 engage opposing sides of cover plates 12, 14. To faciliate the engagement of the opposing sides of clamp portion 42 to opposing sides of cover plates 12, 14, clamp portions 42 are preferably provided with upturned flange portions 44. Flange portions 44 may be shaped as necessary to allow clamp portions 42 to slide onto the opposing surfaces of cover plates 12, 14 and to avoid a conflict with other portions of perfusion slit chamber 10, such as valve assemblies 22, 24. Such a shaped flange portion 44 is indicated as 45 in FIG. 6.

In FIG. 1, four clamping assemblies 34 are shown; however, in alternate embodiments of the invention, fewer clamping assemblies 34 could be used. For example, a pair of clamping assemblies 34 on opposing sides of perfusion slit chamber 10 with clamping posts 36 mounted, for example, on opposing corners of cover plates 12, 14 could satisfactorily close and hold cover plates 12, 14 together.

In the preferred embodiment, perfusion slit chamber 10 includes a plurality of heat exchanger fins 46 on each of first and second cover plates 12, 14. Heat exchanger fins 46 are arranged to extend outward of treatment chamber 16 from cover plates 12, 14 and are conveniently molded or machined from the same piece of material used to construct first and second cover plates 12, 14. The particular arrangement of heat exchanger fins 46 shown in FIG. 1 is convenient, but other arrangements will be apparent to those skilled in the art. The function of heat exchanger fins 46 is to strengthen first and second cover plates 12, 14 while simultaneously allowing rapid equilibrium of the temperature of treatment chamber 16 with the ambient.

Perfusion slit chamber 10 is shown in exploded perspective view in FIG. 2, in which the assembly of perfusion slit chamber 10 is also indicated. Cover plates 12, 14 are mated together over a filter or membrane sheet 48, which is thereby enclosed within treatment chamber 16. As also shown in FIG. 2, the preferred perfusion slit chamber 10 includes a sealing O-ring 50 set into an O-ring groove 52 in a known to those skilled in the art. In the preferred perfusion slit chamber 10, O-ring groove 52 is inscribed into one of cover plates 12, 14; in alternate embodiments, an analogous O-ring groove 52 could be inscribed into each of cover plates 12, 14. Although cover plates 12, 14 are sealingly engaged with O-ring 50 in the preferred embodiment, in alternate embodiments, other types of sealing gaskets and arrangements could be used. Since perfusion slit chamber 10 is operated without significantly elevated pressures or high vacuums, O-ring 50 need not be able to withstand high pressure differentials between the ambient and treatment chamber 16, although O-ring 50 will be sufficient to prevent introduction of contaminants from the ambient into treatment chamber 16 and to substantially prevent the escape of radioactive and other reagents from treatment chamber 16. O-ring 50 can be made of silicon rubber or other suitably inert, pliable material.

In the preferred perfusion slit chamber 10, each cover plate 12, 14 is provided with a generally rectagonal recess 53. In FIG. 2, recess 53 is seen most clearly on second cover plate 14. The opposing recess 53 in cover plate 12 is analogous to that shown in cover plate 14. When first and second cover plates 12, 14 are mated together, recesses 53 cooperate to form treatment chamber 16. In alternate embodiments of the invention, a single recess 53 could be inscribed in one of cover plates 12, 14.

Each cover plate 12, 14 is also provided with a baffle 54 and a slot 56. In FIG. 2, only baffle 54 and slot 56, provided on cover plate 14, are shown. Baffle 54 is located near bottom 30, while slot 56 is located near top 32. Baffle 54 and slot 56 of cover plate 12 are analogous to those shown with cover plate 14; however, baffle 54 on cover plate 12 is located near top 32, and slot 56 on cover plate 12 is located near bottom 30. In this manner, when perfusion slit chamber 10 is assembled, baffle 54 of each cover plate 12 or 14 fits into the corresponding slot 56 of the other cover plate 12, 14. Baffles 54 and slots 56 are located such that one baffle 54 is interposed between each reagent port 18, 20 and the majority of treatment chamber 16. For the purposes of discussion, the reagent of treatment chamber 16, located between baffles 54, will be referred to as filter/filter region 58. Baffles 54 serve to distribute reagents entering treatment chamber 16 through reagent ports 18, 20 in laminar fashion over the entire width of filter region 58, and will be described more fully below in conjunction with the discussion of FIG. 5.

Filter or membrane sheet 48 is, in the assembled perfusion slit chamber 10, located in filter region 58 between baffles 54. To hold filter or membrane sheet 48 away from the walls of cover plate walls 60, 62, cover plates 12, 14 are provided in filter region 58 with a plurality of filter support pegs 64 to allow reagents to flow essentially unimpeded on either side of filter or membrane sheet 48 with each port communicating with both sides of the membrane. Several filter support pegs 64 are shown in detail in FIG. 4. Preferably, in the preferred perfusion slit chamber 10, filter support pegs 64 are positioned such that pairs of support pegs 64 projecting from cover plates 12, 14 oppose each other with a gap between opposing support pegs 64, which is somewhat wider than the width of paper or membrane sheet 48. Arranging opposing pairs of support pegs 64 substantially prevents wadding or creasing or slippage of filter or membrane sheet 48 while the preferred gap between opposing support pegs 64 allows some freedom of movement of sheet filter or membrane sheet 48 and allows sheet 48 to be evenly exposed to reagents in treatment chamber 16. While other placements of opposing pairs of support pegs 64 are contemplated to be within the scope of the invention, it has been empirically found that positioning support pegs 64 such that pairs of support pegs 64 are opposed also leads to more even contact of sheet 48 with reagents in treatment chamber 16, and hence better images and detection of the DNA/DNA, DNA/RNA, and protein complexes on sheet 48.

A cross-sectional view of perfusion slit chamber 10, taken along section 3—3 of FIG. 1, is shown in FIG. 3. FIG. 3 shows the cooperation of recesses 53 to form treatment chamber 16 and filter region 58. FIG. 3 also shows the cooperation of baffles 54 with slots 56.

Also shown in FIG. 3 are reagent paths 26, 28. Reagent path 28 fluidly communicates with treatment chamber 16 via reagent port 20 and with valve assembly 24. The direction of flow of reagent indicated in FIG. 3 through reagent path 28 is for withdrawal of reagent through valve assembly 24, although each valve assembly 22, 24 can be used alternately for introduction and removal of reagent from treatment chamber 16. Reagent path 26 provides for fluid communication from valve assembly 22 to treatment chamber 16 via reagent port 18. Valve assembly 22 is not shown in FIG. 3, but is shown in FIGS. 1 and 5.

Reagent paths 26, 28 are conveniently defined utilizing first and second flow path covers 70, 72. For manufacturing convenience, it is desirable to construct cover plates 12, 14 identically except for baffles 54, slots 56, O-ring groove 52, and reagent ports 18, 20. To this end, cover plates 12, 14 are formed to have Y-shaped channels indicated generally as 76 in FIG. 5. Two legs of the Y-shaped channel 76 lead respectively to the regions in which reagent ports 18, 20 will be formed. The third leg of the "Y" communicates to the corresponding valve assembly 22, 24. Flow path covers 70, 72 are constructed to fit over Y-shaped channels 76 to form the appropriate reagent path 26 or 28. Each of flow path covers 70, 72 has a flow path plug 78, 80, which is inserted in the appropriate leg of the Y-shaped channel 76 to direct flow to reagent port 18 or 20, respectively. Plug 78 is formed to extend from flow path cover 70 to fit in one leg of Y-shaped channel 76 to divert flow to reagent port 18 near bottom 30., Plug 78 is shown in FIG. 5. To form reagent path 28, plug (not shown in FIG. 5) is appended from flow path cover 72 to project into and block one leg of Y-shaped channel 76 between the intersection of the "Y" and bottom 30. Thus, when flow path cover 72 is assembled with cover plate 14, reagent introduced via valve assembly 22 is diverted towards top 32 through reagent port 20. Reagent flow exiting reagent port 20 into treatment chamber 16 is shown in phantom in FIG. 5. Utilizing flow path cover 70, 72, much of the manufacture of cover plates 12, 14 is simplified since substantially identical Y-shaped channels 76 can be formed into each of cover plates 12, 14; the particular reagent path 26 or 28 is then determined by the location of plug 78 or 80 on flow path covers 70 or 72, respectively.

Figure 5:
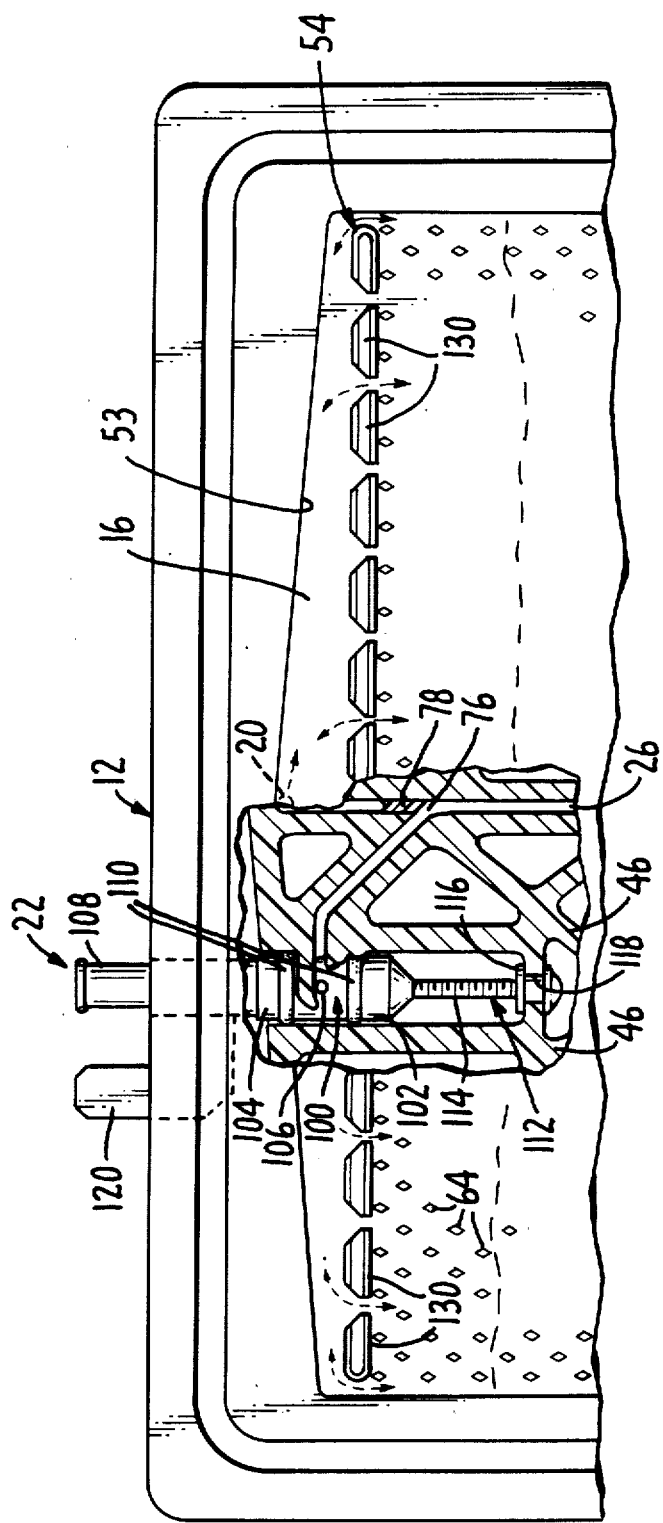
FIG. 5 is a cutaway plan view of the preferred perfusion slit chamber showing one set of fluid distribution baffles and, schematically, the fluid flow therethrough, and including in cutaway, a detail of one of the valve assemblies.

The details of valve assembly 22 are shown in FIG. 5. The details of valve assembly 24 are not separately shown, but are substantially the same as those of valve assembly 22, and the discussion below of valve assembly 22 is equally applicable to valve assembly 24. Valve assembly 22 includes a valve stem 100 and a valve seat 102. Valve seat 102 is conveniently formed in the same piece of material used to form cover plate 12 and is shaped to accommodate valve stem 100. Valve stem 100 is rotatable within valve seat 102 and includes a valve body 104, a valve port 106, a syringe mount 108, and a pair of O-rings 110. Valve body 104 is generally cylindrical and, in the preferred embodiment, grooved around its circumference to accommodate O-rings 110 in a manner well known to those skilled in the art. Valve body 104 also includes an angled valve bore (not shown) to fluidly couple valve port 106 to syringe mount 108. O-rings 110 are positioned above and below valve port 106, and sealingly but rotatably engage valve seat 102 to prevent leakage. Other means of sealingly and rotatably engaging valve stem 100 to valve seat 102 will be apparent to those skilled in the art. Syringe mount 108 is preferably a standard syringe mounting, such as a "LUER LOK" mount of the type which will be well known to those skilled in the art. Other means of coupling a syringe or other reagent delivery device to valve assembly 22 will be apparent to those skilled in the art.

Valve stem 100 is adjustably positioned within valve seat 102 using a positioner 112. Positioner 112 includes a screw 114, a bearing 116, and, defined within an appropriately positioned heat exchanger fin 46, a bearing mount 118. Typically, bearing mount 118 is a slot cut into the appropriately positioned heat exchanger fin 46 for sliding engagement of bearing 116. Screw 114 is threadedly engagable into a matching hole (not shown) in the end of valve stem 100 and passes through bearing 116. Screw 114 can be adjusted to locate valve port 106 at a location corresponding to the appropraite leg of Y-shaped channel 76. In alternate embodiments of the apparatus, screw 114 and bearing 116 can be made as an integral portion of valve stem 100, albeit without adjustability.

Valve stem 100 is conveniently made manually rotatable within valve seat 102 with a tab 120. Tab 120 is fixedly mounted to valve stem 100 to extend to one side therefrom. Other suitable means for rotating valve stem 100 will be apparent to those skilled in the art. In the position of valve stem 100, valve port 106, and tab 120, shown in FIG. 5, valve port 106 is positioned to fluidly communicate with reagent path 26. When valve stem 100 is rotated away from the position shown in FIG. 5, using tab 120, valve port 106 is rotated away from reagent path 26 to control or stop flow of reagent through reagent path 26.

Valve stem 100 is conveniently made from a plastic material such as Delrin, and is sized such that a tight slip fit is formed between valve stem 100 and valve seat 102. Thus, when valve stem 100 is in a position which located valve port 106 away from reagent path 26, the flow of reagent through reagent path 26 is effectively stopped. O-rings 110 assure a leakage-tight fit between valve stem 100 and valve seat 102.

One baffle 54 is also shown in FIG. 5. Baffle 54 includes a plurality of tongues 130 shaped to relatively tightly fit into the corresponding slot 56 and variably spaced to extend across the width of a treatment chamber 16. Generally, the gaps between adjacent tongues 130 increase as the distance from the corresponding reagent port 20 or 22 (reagent port 20, in FIG. 5) increases. That is, the gaps between adjacent tongues 136 are smaller near the center of treatment chamber 16 and wider near its edges. The spacing corresponds approximately to that which would be predicted by Bernoulli's theorum, and is empirically adjusted such that the flow into filter region 53 is approximately constant over the entire width of filter region 53. The gaps between adjacent tongues 130 extend across the entire depth of treatment chamber 16 and the filter region 53, so that reagent is evenly distributed to both sides of filter or membrane sheet 48.

Although the operation of perfusion slit chamber 10 can be inferred from the above description of the preferred apparatus according to the invention, for clarity a description of a typical procedure for using perfusion slit chamber 10 will now be given.

The filter or membrane sheet 48 with the polynucleotide or protein of interest, bound or blotted onto sheet 48, is placed between cover plates 12, 14. If sheet 48 is dry and is of a type which expands upon moistening, it is convenient to premoisten the dry sheet 48 prior to assembly of perfusion slit chamber 10. The disassembled perfusion slit chamber 10 is assembled as indicated in FIG. 2 with sheet 48 between cover plates 12, 14 and filter region 53. Cover plates 12, 14 are clamped with clamping assemblies 34 and, if required by the reagents to be used, perfusion slit chamber 10 is positioned with top 32 up in a water bath of the appropriate temperature. Approximately 25 ml of prehybridization solution (preheated to appropriate temperature) is drawn into a 35 ml capacity syringe, which is, in turn, mounted to, for example, syringe mount 108 of valve assembly 22. A second, empty, closed syringe of similar capacity is mounted to the other of valve assemblies 22, 24. Both valve assemblies 22, 24 are opened and the prehybridization solution is injected into treatment chamber 16. If necessary, the prehybridization solution can be drawn through treatment chamber 16 by withdrawing the plunger of the second syringe. The prehybridization solution is then pushed back and forth from one syringe to the other through treatment chamber 16 until no air bubbles adhere to the membrane. Valve assemblies 22, 24 are then closed and perfusion slit chamber 10 is incubated, as necessary. A prehybridization solution comprising 1.0 M NaCl, 1.0% SDS (sodium dodecyl sulfate) and a nylon-66 sheet 48, incubation at 65° C. for one to three hours has been found to be acceptable.

Following prehybridization treatment of sheet 48, and with perfusion slit chamber 10 positioned such that valve assemblies 22, 24 extend above the surface of the water in the water bath, valve assemblies 22, 24 are opened after the syringes are mounted. The prehybridization solution is removed from treatment chamber 16, again using two syringes, and an appropriate hybridization solution is injected into treatment chamber 16 using a technique similar to that for injection of the prehybridization solution. Any of the wide variety of known hybridization solutions can be used, according to the methodology being performed. A typical hybridization solution comprises approximately 10% dextran sulfate, 1.0 M NaCl, 1% SDS, and 100 mg/μl of denatured heterologous DNA. Additionally, a DNA or RNA species in the hybridization solution will be radioactively labeled with a specific radioactivity of at least $1 \times 10^8$ cpm/μg DNA. The hybridization solution is introduced into perfusion slit chamber 10 and is "washed" from one syringe to the other to ensure removal of all air bubbles from treatment chamber 16 and to maximize contact between the hybridization solution and filter or membrane sheet 48. After closing valve assemblies 22, 24 and removing the syringes, perfusion slit chamber 10 is again incubated at the required temperature for, e.g., 18 to 48 hours. The length of the incubation time depends upon such factors as the specific activity of the probe DNA, the concentration of DNA immobilized on sheet 48, and the frequency of the particular gene sequence of interest. In general, perfusion slit chamber 10, loaded with hybridization solution, should be incubated for one to three times the half-life of the binding reaction between the probe DNA and the immobilized DNA.

After sufficient incubation, syringes are again used to withdraw the hybridization solution from treatment chamber 16 via reagent port 18 (located near bottom 30). This procedure allows essentially spill-proof withdrawal of the radioactive hybridization solution from perfusion slit chamber 10 into the syringe for safe disposal.

The now hybridized sheet 48 is then washed in a manner analogous to the method for introducing prehybridization solution and hybridization solution using successive washes of increasing stringency. For example, a Standard Saline Phosphate EDTA (IX SSPE) solution containing 0.18 M NaCl, 0.01 M NaPO$_4$ buffer (pH 7.4), and 1 mM EDTA (pH 7.4) has been found suitable. The hybridized sheet 48 is washed with successively higher stringency wash solutions. A typical low stringency wash consumes approximately 100 ml of 2X SSPE/1% SDS solution. A typical moderate stringency wash solution consumes about 50 ml of 0.5X SSPE/1% SDS, and a typical high stringency wash solution consumes about 25 ml of 0.1X SSPE/1% SDS. For each wash solution, approximately 35 ml of the appropriate wash solution is introduced into treatment chamber 16 using syringes as for introduction of the prehybridization and hybridization solutions, and repeatedly transferred between syringes. About 10–20 seconds of transfer of the wash solution will remove essentially all unbound radioactivity from sheet 48 and treatment chamber 16. This initial low stringency wash is removed and properly disposed of.

Perfusion slit chamber 10 is again filled with low stringency wash and air bubbles are removed by repeatedly transferring the wash solution between the two syringes. After closing valve assemblies 22, 24, perfusion slit chamber 10 is incubated at, e.g., 65° C. for 30–60 minutes. This procedure is repeated with moderate and high stringency wash solutions. The temperature and salt concentration of the final wash solution should be chosen so that the incubation temperature is about 5°–8° C. below the $T_m$ of the hybrid understudy.

Although not ususally necessary, wash solutions can be rapidly screened with a Geiger counter to assess completion of the washing.

Perfusion slit chamber 10 is next disassembled after removal of the final, high stringency wash solution. The treated sheet 48 is removed, blotted, and enclosed, still damp, in, e.g., plastic wrap. In a darkroom, the wrapped sheet 48 is sandwiched between two sheets of x-ray film. The sandwiched sheet 48 is incubated at, typically, −70° C. for one to five days prior to development of the x-ray films.

While the above is a complete description of the preferred embodiment of the invention, other arrangements and equivalents are possible and may be employed without departing from the true spirit and scope of the invention. Many such alternate arrangements and equivalents have been suggested above; others will be apparent to those skilled in the art. Therefore, the description and illustrations should not be construed as limiting the scope of the invention, which is delineated by the appended claim.

What is claimed is:

1. An apparatus for treating samples bound to a support membrane and the like with a solution without pumping the solution through the membrane, the apparatus comprising:

first and second cover plates, at least one of the first and second cover plates having a recess defined on one side thereof, the cover plates being matable to form a treatment chamber therebetween;

a membrane supported in the chamber;

first and second reagent ports defined in at least one of the first and second cover plates for fluidly communicating into and alternatively out of the treatment chamber with each port communicating with both sides of the membrane;

first and second valve means for controlling fluid communication through the first and second reagent ports, respectively, to the treatment chamber;

clamping means for releasably securing the mater cover plates together;

passageway means extending through the chamber along both sides of the memberane for providing bilaminar flow along the faces of a membrane in the treatment chamber without pumping substantial quantities of solution through the membrane; and internal of the treatment chamber, a plurality of support pegs affixed to the cover plates for supporting the membrane and allowing solution flow on each side of the membrane from the first reagent port to the second reagent port.

2. The apparatus of claim 1 in which said chamber has a central area thereof receiving the membrane and containing the support pegs;

said first and second reagent ports are located on opposite sides of said central area; and first and second resistance baffles are mounted in said chamber between said central area and between said first and second reagent ports for providing bilaminar flow through said central area of said chamber.

3. The apparatus of claim 2 in which the chamber completely surrounds the membrane with the membrane unattached to the cover plates whereby the solution circulates around the membrane without flowing through the membrane.

* * * * *

UNITED STATES PATENT AND TRADEMARK OFFICE
CERTIFICATE OF CORRECTION

PATENT NO. : 4,681,853

DATED : July 21, 1987

INVENTOR(S) : Kenneth J. Hardy et al.

It is certified that error appears in the above-identified patent and that said Letters Patent is hereby corrected as shown below:

On the Title Page add,--[73] Assignee: Hoefer Scientific
  Instruments, a Corp. of CA --.

Signed and Sealed this

Fourteenth Day of June, 1988

Attest:

DONALD J. QUIGG

*Attesting Officer*     *Commissioner of Patents and Trademarks*